US006368555B1

(12) United States Patent
Goeldner

(10) Patent No.: US 6,368,555 B1
(45) Date of Patent: Apr. 9, 2002

(54) METHOD FOR TREATING CONTAMINATED MATERIAL, SPECIFICALLY INFECTED MATERIAL

(76) Inventor: Helmut Goeldner, Gewerbegebiet Oehmer Feld, 31633 Leese (DE)

( * ) Notice: Subject to any disclaimer, the term of this patent is extended or adjusted under 35 U.S.C. 154(b) by 0 days.

(21) Appl. No.: 09/403,809
(22) PCT Filed: Apr. 21, 1998
(86) PCT No.: PCT/EP98/02371
§ 371 Date: Feb. 10, 2000
§ 102(e) Date: Feb. 10, 2000
(87) PCT Pub. No.: WO98/48853
PCT Pub. Date: Nov. 5, 1998

(30) Foreign Application Priority Data

Apr. 26, 1997 (DE) .......................................... 197 17 839

(51) Int. Cl.[7] ................................................ A61L 2/08
(52) U.S. Cl. ........................ 422/26; 422/307; 422/308; 422/309; 422/295; 198/657; 432/107
(58) Field of Search ......................... 422/26, 258, 307, 422/308, 295, 309; 432/107; 99/443 R; 198/657

(56) References Cited

U.S. PATENT DOCUMENTS 3,464,342 A * 9/1969 Kleinkauf ..................... 99/443
4,701,266 A * 10/1987 Janka et al. ................. 210/803
4,993,943 A * 2/1991 Norris et al. ................ 432/107

OTHER PUBLICATIONS

Nadirov et al., Feb. 1991, Derwent Abstract of SU 1603844 A.*

* cited by examiner

Primary Examiner—Robert J. Warden, Sr.
Assistant Examiner—Sean E. Conley
(74) Attorney, Agent, or Firm—Crowell & Moring LLP

(57) ABSTRACT

The invention relates to a method and device for treating contaminated materials, specially infected materials, which are fed to endless screws (5, 12) via a feed hopper (2) and are heated, disinfected or sterilized in addition to being discharged through an ejection system (21). The invention is characterized in that the materials are supplied to a first endless screw which is configured as a heating screw (5), wherein the material is also compacted in such a way that a sealing material plug (25) is produced at the end of said screw; the material is released into a treatment chamber (8) at the end of the heating screw (5) where it is expanded; the material in the treatment chamber (8) travels to a second endless screw which is configured as a treatment screw (12); burst of energy are introduced into the treatment chamber (8) into the treatment screw (12) in a controlled manner, steam is supplied or generated and an overpressure and the required temperature are produced and maintained and the material is compacted at the end of the treatment screw (12) into a second sealing material plug (26) so that the overpressure between both sealing material plugs (25, 26) of the screws (5, 12) can be maintained during a specific period of time. One advantage of the invention is that this method enables overpressure to be maintained between both high-sealing material plugs, which are continuously and automatically formed, over a long distance during a specific period of time.

30 Claims, 3 Drawing Sheets

METHOD FOR TREATING CONTAMINATED MATERIAL, SPECIFICALLY INFECTED MATERIAL

The invention relates to a method and an apparatus for the treatment of contaminated, especially infected materials, in which the latter are fed through a feed hopper to a screw conveyor, heated and disinfected or sterilized, and emptied through a discharge.

A high-temperature disinfection apparatus for hospital wastes has been disclosed by DE 39 38 546 C2, in which the wastes are fed through a feed hopper to two screw conveyor sections separated by pressure-tight mechanical locks. In the first screw conveyor section a steam pressure is adjustably produced by heat input, while in the second screw conveyor section a vacuum is produced in order to remove moisture from the material by drawing off the vapors. In this known apparatus it is a disadvantage that mechanical pressure locks are used, which are complicated and also give trouble. Since leakage must always be expected, such mechanical pressure locks are not suitable for assuring the pressure conditions necessary for disinfection. In addition, the screw system sections are arranged in the horizontal plane, so that contaminated fluid can flow unnoticed through the apparatus and pass through this process untreated or improperly treated. There is no assurance that under all conditions a reliable disinfection, and especially sterilization of the wastes, will be accomplished.

The invention is based on the object of providing a process and an apparatus which by using simple technical means will always assure a reliable disinfection and sterilization of contaminated materials, and in which energy consumption will also be optimized.

This object is achieved in accordance with the invention by the features of claim 1, as well as of claim 16. Further description of the invention will be found in the dependent claims.

Since the materials are fed to a first screw conveyor which is configured as a heating screw conveyor wherein a compression of the material takes place such that a sealing plug of material is produced in its end area, the material is released at the end of the heating screw conveyor into a treatment chamber and expands therein, the material in the area of the treatment chamber passes into a second screw conveyor which is configured as a treatment conveyor, controlled bursts of energy are introduced into the treatment conveyor, steam is delivered or produced and an excess pressure and the necessary temperature are built up and maintained, and in the end part of the treatment screw conveyor the material is compressed to form a second, sealing plug of material, it has been accomplished that, between the two constantly and automatically forming plugs of material providing a good seal, an excess pressure that is very advantageous to the process can be maintained over a long path for a defined period of time.

Preferably, the material in the heating screw conveyor, which is arranged to feed upward at an angle, is transported upwardly. This reliably prevents contaminated fluid from the area below the feed hopper from flowing unnoticed into the apparatus and possibly passing through the process untreated or improperly treated. The angle of inclination of the heating conveyor from the horizontal plane is as a rule between 20° and 45°.

Preferably, saturated steam is introduced in bursts into the treatment chamber and into the treatment screw conveyor. Injection in bursts achieves a pressure increase and a depth effect, since between the bursts of steam an expansion, especially of the material in the treatment chamber, is produced. An equal effect is achievable if microwave energy is introduced in bursts into moist material in the treatment chamber and/or the treatment conveyor.

It is provided within the scope of the invention that at the entrance into the heating screw conveyor a moisture sensor will measure the moisture content of the material, and that water will be added to the material in the necessary proportion, if required.

It is advantageous if, at the end of the heating screw conveyor the temperature of the material is measured and the driving means of the heating screw conveyor is controlled according to the temperature measured such that the holding time of the material in the screw conveyors and in the treatment chamber is assured.

Furthermore, provision is made so that a temperature sensor will track the temperatures occurring in the area at the entrance of the treatment conveyor and record and document them by means of a recording apparatus, so that the temperature program will be reproducible afterwards. It is thus possible to have proof even very much later that the material was treated as prescribed. If in the rear area of the treatment conveyor a temperature sensor is disposed by which the temperature of the material in this area is tracked and recorded by means of a recording apparatus it will be possible to evaluate the data in comparison with the recording made by the temperature sensor in the entry area of the treatment conveyor.

It may be advantageous if a conical ring is disposed in the end area of the heating screw conveyor and of the treatment conveyor to promote the compression of the material and the formation of the sealing plugs. An expansion of the material will then take place behind the ring.

In a preferred embodiment of the invention, the compression of the material is performed in the area of the screw conveyor and/or the treatment conveyor by means of a transport spiral. Here an especially good and safe formation of the sealing plug can be achieved, since on account of the lack of an internal worm shaft the material is driven with special intensity in the end area of the conveyors, where it is intensely compressed. This effect can be enhanced by performing the compression of the material in the screw conveyor and/or the treatment screw conveyor such that the pitch of the transport spiral decreases in the end area.

Within the scope of the invention it is also provided that, by means of a retention flap arranged at the end of the treatment conveyor an additional compression of the material occurs. Insofar as the additional compression is effected by means of a multi-part retaining flap, a continuously operating supplemental throttle gap is maintained.

Also it is advantageous if vapors emitted in the area of the discharge are sucked away by means of a suction duct.

A further optimization of the method of the invention is possible if a temperature sensor is disposed in the treatment chamber or in the inlet of the treatment conveyor by means of which the treatment temperature of the material is detected and the driving means of the treatment conveyor is regulated so as to maintain the optimum treatment temperature and treatment time.

The apparatus of the invention is furthermore characterized in that a first screw conveyor is provided which is configured as a heating screw conveyor surrounded by a heating element and in which a compression of the material takes place such that a sealing plug of material is produced in its end region, that at the end of the first screw conveyor a treatment chamber is disposed in which an expansion and loosening of the structure of the material takes place, that a second screw conveyor configured as a conveyor surrounded by a heating element for the material reaches into the treatment chamber, that energy bursts can be introduced into the treatment chamber and into the treatment conveyor, steam is delivered and/or produced, and an elevated pressure and the necessary temperature are built up and maintained, and that the treatment screw compresses the material in its end region to form a second sealing plug of material, such that the elevated pressure can be maintained for a defined period of time between the two material plugs of the screw conveyors which act as seals.

Within the scope of the invention provision is made for the heating screw conveyor and/or the treatment screw conveyor to be formed by a transport spiral which is mounted on slide rails extending lengthwise along the inner walls of the screw housing. In that case it can be advantageous if the pitch of the heating screw conveyor and/or of the treatment screw is reduced in the end regions thereof.

In accordance with one preferred embodiment of the invention, the heating screw conveyor is arranged in the apparatus extending at an upward angle in the direction of flow. This prevents unacceptably large amounts of liquid from being fed into the treatment chamber or into the treatment screw. Preferably the heating screw conveyor is oriented at an upwardly inclined angle of 20 to 45°.

In the drawing an embodiment of the invention is illustrated and will be described in further detail below.

Figure 1:
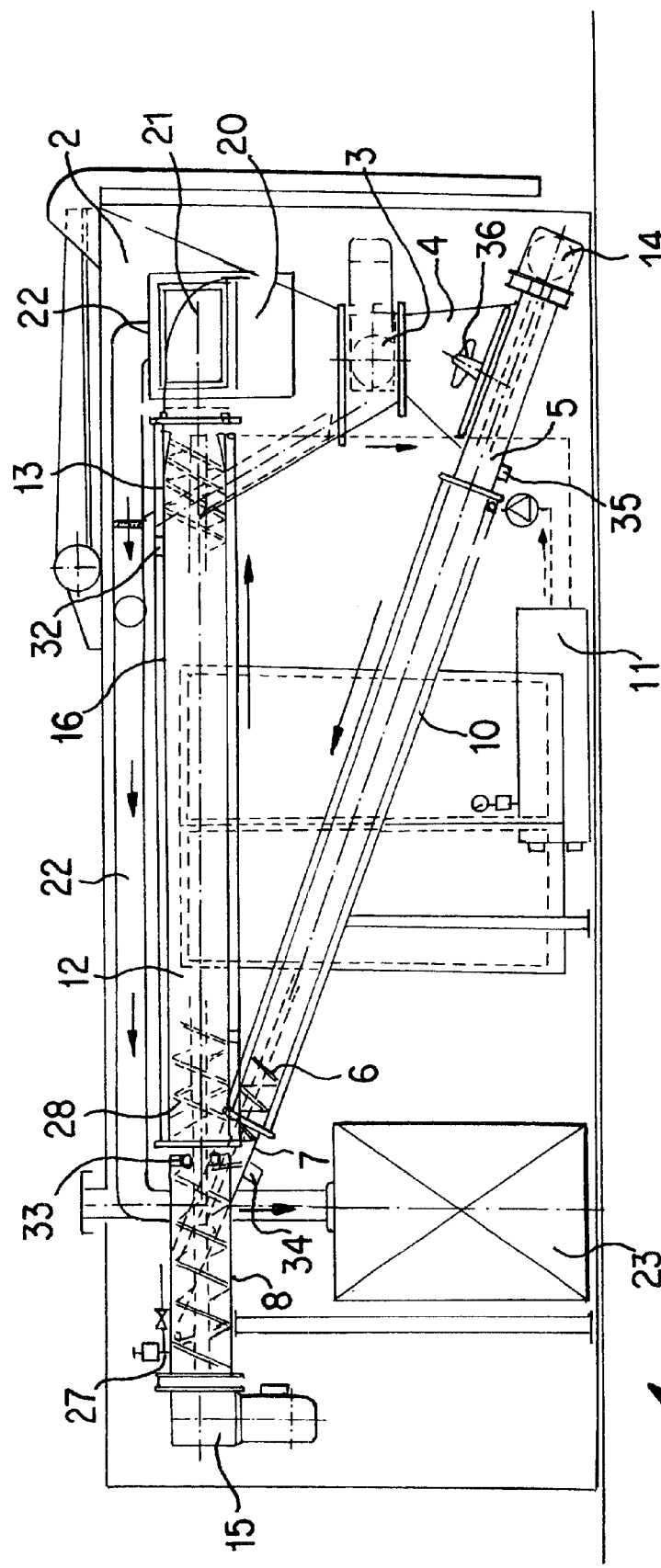
FIG. 1 shows a schematic side view of an apparatus.
Figure 2:
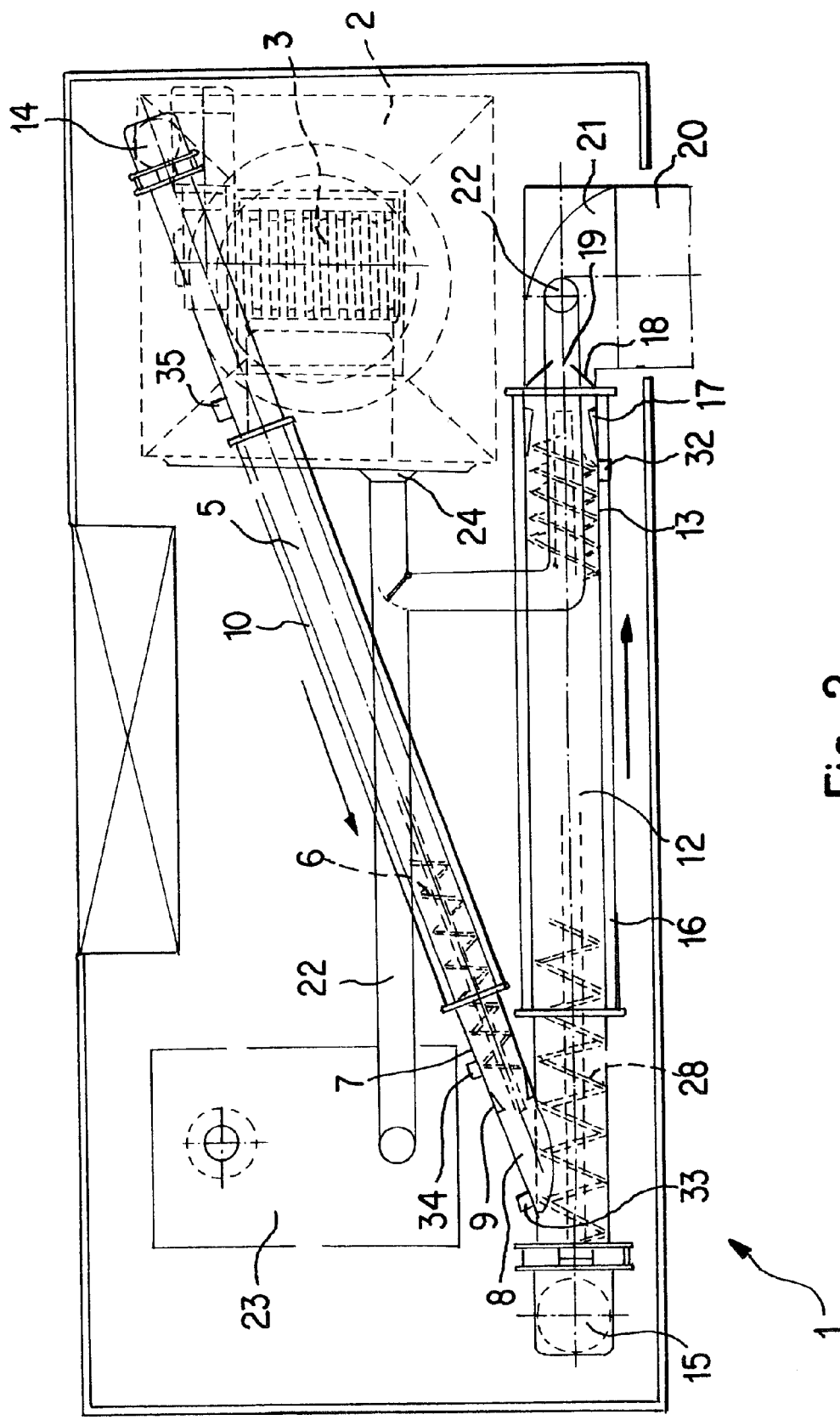
FIG. 2 shows the apparatus of FIG. 1 in a top plan view.

In the drawing an apparatus for the treatment of contaminated, especially infected, materials is identified by the numeral 1. The apparatus 1 has a feed hopper 2 under which a size reduction mill 3 is disposed. From the mill 3 a shaft 4 leads to a first screw conveyor which is constructed as a heating screw conveyor 5. The heating screw conveyor 5 is arranged at an inclined angle relative to a horizontal plane, which is about 30°. The heating screw conveyor 5 has a transport spiral 6 which has an end region 7 which opens into a treatment chamber 8. In the end portion 7 of the heating screw conveyor 5, a conical ring 9 is disposed.

The heating screw conveyor 5 is provided over most of its length with a double jacket 10 in which there is a heat transfer oil which is heated in a heating block 11. The heating screw conveyor 5 furthermore is oriented with an upward inclination in its direction of conveyance leading to the treatment chamber 8 of the apparatus 1. The angle of inclination of the heating screw conveyor from the horizontal plane is advantageously between 20° and 45°. The transport spiral 6 of the heating screw conveyor 5 furthermore has a reduced pitch in its end region 7.

The treatment chamber 8 of apparatus 1 runs to a second screw conveyor which is designed as a treatment conveyor 12. The treatment screw conveyor 12 has a transport spiral 28 which has a reduced pitch in an end region 13 of the treatment screw conveyor 12. The heating screw conveyor 5 and the treatment screw conveyor 12 are driven by drives 14 and 15.

The treatment screw conveyor 12 is also provided with a double jacket 16 which extends over most of its length and is filled with a heat transfer oil. This heat transfer oil also is heated in the heating block 11. A conical ring 17 is disposed within the treatment screw conveyor 12 in its end region 13. The end region 13 is closed off by a retaining flap 18 which here forms a throttling gap 19. The retention flap 18 of the treatment screw conveyor 12 is adjoined by a discharge 21 with a chute 20. In the vicinity of the discharge 21, a suction duct 22 is disposed which leads to a filter system 23. An additional connection 24 of the suction duct 22 leads to the feed hopper 2.

In the end region 7 of the heating screw conveyor 5 a sealing plug 25 about 100 to 200 mm long is formed from the material when the apparatus 1 is in operation. Also in the end region 13 of the treatment screw conveyor 12 a sealing plug of material 26 is formed. In the area of the treatment chamber 8 an inlet 27 for saturated steam is provided.

Figure 3:
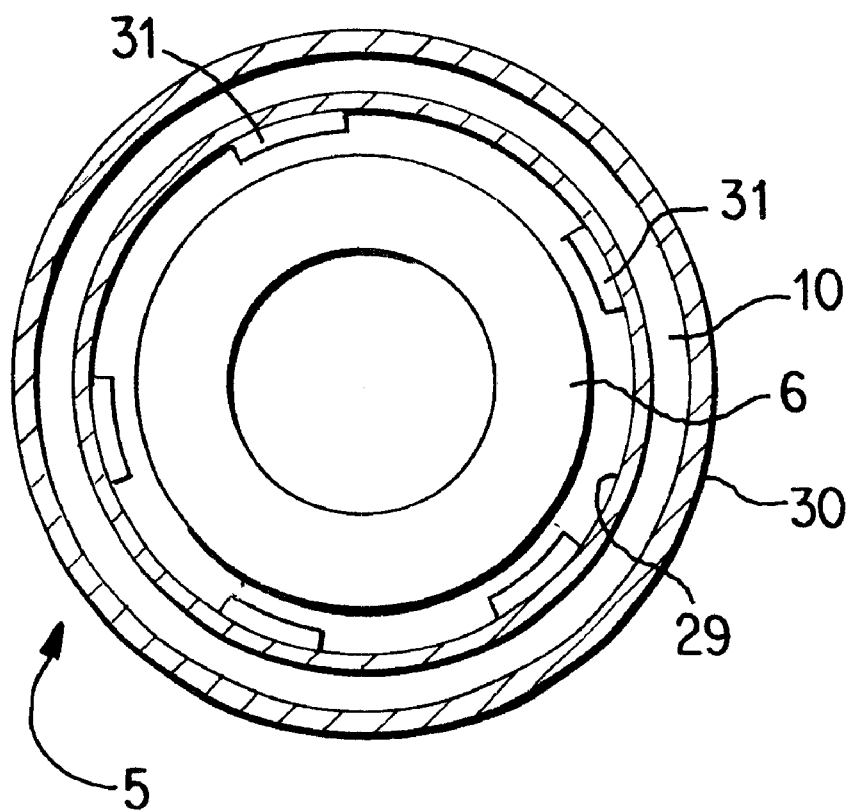
FIG. 3 shows the heating screw conveyor in cross section.

As can be seen in FIG. 3, the transport spirals 6 and 28 of the heating screw conveyor 5 and treatment screw conveyor 12 are mounted on slide rails 31 extending lengthwise along the inner walls 29 of the screw conveyor housing 30. As an additional effect the slide rails 31 produce an advantageous shearing and positive conveyance of the transported material.

A temperature sensor 32 is disposed in the rear region of the treatment screw conveyor 12. An additional temperature sensor 33 is disposed in the area of the treatment chamber 8. Also, a temperature sensor 34 is disposed at the end of the heating screw conveyor 5. A moisture sensor 35 is arranged at the inlet of the heating screw conveyor 5.

In order to treat contaminated materials, the material is fed to the apparatus 1 through the feed hopper 2. The size reduction mill 3 chops the material to a size of preferably 10×20 mm, while hollow articles such as syringes are destroyed. The material is then conveyed through the shaft 4 to the heating screw conveyor 5. The interposed feeder 36 provides for an optimum fill level in the heating spiral.

In the heating screw conveyor 5 the material is transported, heated to about 105° C. and compressed. Since the heating screw conveyor 5 is disposed at an angle of about 30° to the horizontal plane, an upward feed of the material results. This reliably prevents contaminated fluid from the area beneath the feed hopper 2 from flowing unnoticed into the apparatus and from passing through the process untreated or insufficiently treated.

The shaftless transport spiral 6 carries the material over a prescribed length into the treatment chamber 8. Since the heating screw conveyor 5 is heated by the heat transfer oil in its double jacket 10, the material in the heating screw conveyor 5 also is heated to a specified temperature. It is important that the material in the end region 7 of the heating screw conveyor 5 is compressed to form a plug 25 of material. The conical ring 9 disposed in this area assists in this compression of the material. Moreover, the decreasing pitch of the transport spiral 6 in the end portion 7 promotes the compression of the material.

Following the conical ring of the heating screw conveyor 5 there occurs a loosening of the material which passes into the treatment chamber 8. Saturated steam is fed in bursts into the treatment chamber 8 and an elevated pressure and the necessary temperature are built up and maintained. The steam phases preferably comprise about two minutes of steaming and a pause of one minute each. In particular, any closed hollow bodies contained in the material are broken up by these bursts.

Maintaining the pressure of the saturated steam in the treatment chamber 8 is certainly possible since the sealing plug of material 26 also forms in the end region 13 of the adjoining treatment screw 12. Thus, optimum conditions for disinfection and especially also sterilization of the material can be established in the treatment chamber 8 as well as in the treatment screw conveyor 12. Overall, a very good energy balance results. The saturated steam injected in bursts furthermore produces a compression and advantageous loosening of the material in the treatment chamber 8, so that the steam can thoroughly penetrate the material. Thus the sterilization process is optimized. The saturated steam is furthermore fed to the treatment chamber 8 at the inlet 27.

The material is transported by the treatment screw 12 toward the discharge 21. The transport spiral 28, whose pitch decreases in the terminal portion 13 of the treatment screw 12, thereby compresses the material to a sealing plug of the material. Here too, the conical ring 17 assists in the compression of the material. The throttling gap 19 of the retaining flap 18 additionally aids the compression. The treated material finally passes to the discharge 21 and is carried away through the chute 20. The vapors that form are drawn away through the suction duct 20, and the air is cleaned in the filter system 23. The same applies to the contaminant-laden air withdrawn from the feed hopper 2 through the suction connection 24. Also, an additional heating of the material takes place in the treatment screw 12 via the heat transfer oil in the double jacket 16.

If microwave energy is to be introduced in bursts into the treatment chamber 8 and treatment screw 12 as an alternative, the moisture content of the material can be measured by the moisture sensor 35 disposed at the entrance to the heating screw conveyor 5, and if necessary water can be added to the material as needed. This water then assures the formation of a sufficient amount of steam when the next introduction of energy is made.

By means of a temperature sensor 33 disposed in the area of the treatment chamber 8 or at the inlet of the treatment screw conveyor 12, the temperatures occurring during the treatment of the material can be tracked and stored and documented by means of a recording apparatus not shown in the drawing. It is thus possible to monitor the course of the temperature at any time and even a great deal later.

By means of the temperature sensor 32 disposed in the end region 7 of the treatment screw 8 it is possible to also measure the temperature of the material in this area, and record it by means of a recording instrument not shown in the drawing. Thus, for example, it is possible to evaluate the data in comparison with the recordings of the temperature sensor 33 in the inlet area of the treatment screw conveyor 12. In particular it is also possible to control the drives 14 and 15 of the heating screw conveyor 5 and treatment screw conveyor 12 so that optimum treatment temperatures and treatment times result.

Overall, the apparatus of the invention is distinguished in that it is a very economical pass-through sterilization system and that due to the two sealing plugs of material 25 and 26, which necessarily form during treatment of the material in the heating screw conveyor 5 and in the treatment screw conveyor 12, optimum safety of operation is achieved. This means that the contaminated materials, which can be preferably hospital-specific wastes, but also clarifying muds, contaminated soils as well as foods, such as grains and spices, can be reliably disinfected and optionally even sterilized. Through the arrangement of a shredder and the delivery of steam in bursts, even the hollow bodies containing fluids which may be present in the material are broken up. Especially also in comparison to an autoclave a very advantageous energy balance is achieved, which is additionally improved since the wastes are already preheated in the heating screw conveyor 5 and the subsequent treatment is effected by saturated steam at elevated pressure over a comparatively very long path and time period in the area between the two material plugs 25 and 26 which seal the system.

What is claimed is:

1. Method for the treatment of contaminated, especially infected materials, in which the materials are supplied through a feed hopper to screw conveyors, heated and disinfected or sterilized, as well as discharged at a discharge, characterized in that the materials are fed to a first screw conveyor which is constructed as a heating screw conveyor, in the heating screw conveyor a compression of the material is additionally performed such that in its end region a sealing material plug is produced, at the end of the heating screw conveyor the material is released into a treatment chamber and expands there, the material in the area of the treatment chamber passes into a second screw conveyor which is constructed as a treatment screw conveyor, energy is introduced in defined bursts into the treatment chamber and into the treatment screw conveyor, steam is supplied or generated and an elevated pressure and the necessary temperature are built up and maintained, in the end region of the treatment screw conveyor the material is compressed to a second sealing material plug such that the elevated pressure can be maintained between the two sealing material plugs of the screw conveyors for a defined period of time.

2. Method according to claim 1, characterized in that the material in the heating screw conveyor, which is arranged inclined upwardly in the direction of conveyance, is transported upwardly.

3. Method according to claim 1, characterized in that saturated steam is introduced in defined bursts into the treatment chamber and into the treatment screw conveyor.

4. Method according to claim 1, characterized in that microwave energy is introduced in defined bursts into the treatment chamber or the treatment screw conveyor.

5. Method according to claim 1, characterized in that the moisture content of the material is measured at the inlet of the heating screw conveyor by means of a moisture sensor and that if needed water is added to the material in a required amount.

6. Method according to claim 1, characterized in that at the end of the heating screw conveyor the temperature of the material is measured and the drive of the heating screw conveyor is controlled depending on the measured temperature such that the residence time of the material in the screw conveyers and in the treatment chamber prescribed for a particular temperature is assured.

7. Method according to claim 1, characterized in that in the area of the treatment chamber or at the inlet of the treatment screw conveyor the temperature is sensed by means of a temperature sensor and stored and documented by means of a recording apparatus, such that the course of the temperature can be subsequently reproduced for control purposes.

8. Method according to claim 1, characterized in that in the end region of the treatment screw conveyor a temperature sensor is disposed with which the temperature of the material in this region is measured and recorded by means of a recording apparatus, such that it is possible to evaluate the data in comparison with the recordings of the temperature sensor at the inlet of the treatment screw conveyor.

9. Method according to claim 1, characterized in that, a conical ring is disposed in the end region of each of the heating screw conveyor and of the treatment screw conveyor, which promotes the compression of the material and the formation of the sealing plug of material.

10. Method according to claim 1, characterized in that the compression of the material in the area of the heating screw conveyor or of the treatment screw conveyor is performed by means of a transport spiral.

11. Method according to claim 9, characterized in that the compression of the material in the heating screw conveyor or in the treatment screw conveyor is effected in that the pitch of the transport spirals decreases in the end region.

12. Method according to claim 1, characterized in that, by means of a retaining flap disposed at the end of the treatment screw conveyor, an additional compression of the material takes place.

13. Method according to claim 11, characterized in that the additional compression is effected by means of a multi-part retaining flap such that an additional throttling gap is continuously maintained.

14. Method according to claim 1, characterized in that vapors emitted in the area of the discharge are drawn away by means of a suction duct.

15. Method according to claim 1, characterized in that in the treatment chamber or in the inlet of the treatment screw conveyor a temperature sensor is disposed by means of which the treatment temperature of the material is sensed and the drive of the treatment screw conveyor is regulated to maintain the optimum treatment temperature and treatment time.

16. Apparatus for treating contaminated, especially infected materials, in which the materials are fed through a feed hopper to a screw conveyor, heated and disinfected or sterilized there, and discharged at a discharge, characterized in that a first screw conveyor is provided, which is constructed as a heating screw conveyor surrounded by a heating element and in which a compression of the material occurs such that a sealing plug of material is produced in its end region, at the end of the heating screw conveyor a treatment chamber is disposed, in which an expansion and loosening of the structure of the material takes place, that into the treatment chamber a second screw conveyor reaches which is constructed as a treatment screw conveyor for the material, surrounded by a heating element, energy can be introduced in defined bursts into the treatment chamber and into the treatment screw conveyor, steam is supplied or generated and an elevated pressure and the necessary temperature are built up and maintained, the treatment screw conveyor compresses the material in its end region to a second sealing plug of material, such that the elevated pressure between the two material plugs which function as seals in the screws can be maintained for a defined period of time.

17. Apparatus according to claim 16, characterized in that the heating screw conveyor is oriented inclined upwardly in the transport direction.

18. Apparatus according to claim 17, characterized in that the heating screw conveyor is oriented inclined upwardly at an angle of 20° to 45°.

19. Apparatus according to claim 16, characterized in that saturated steam can be introduced in defined bursts through an inlet into the treatment chamber and into the treatment screw conveyor.

20. Apparatus according to claim 16, characterized in that microwave energy can be introduced in defined bursts into the treatment chamber or the treatment screw conveyor.

21. Apparatus according to claim 16, characterized in that the heating screw conveyor or the treatment screw conveyor is formed by a transport spiral which is mounted on slide rails extending lengthwise along the inside walls of the screw conveyor housing in the lengthwise direction thereof.

22. Apparatus according to claim 16, characterized in that the pitch of the heating screw conveyor or of the treatment screw conveyor decreases in its end region.

23. Apparatus according to claim 16, characterized in that the heating element of the heating screw conveyor is constructed as a double jacket filled with a heat transfer oil.

24. Apparatus according to claim 16, characterized in that a moisture sensor is disposed at the inlet of the heating screw conveyor such that the moisture content of the material is measurable.

25. Apparatus according to claim 16, characterized in that a temperature sensor is disposed in the end region of the treatment screw conveyor.

26. Apparatus according to claim 16, characterized in that a conical ring is disposed in the end region of each of the heating screw conveyor and of the treatment screw conveyor such that the compression of the material is promoted.

27. Apparatus according to claim 16, characterized in that at the end of the treatment screw conveyor a retaining flap is disposed through which an additional compression of the material is effected.

28. Apparatus according to claim 27, characterized in that the retaining flap is constructed in multiple parts such that a throttling gap is continuously maintained.

29. Apparatus according to claim 16, characterized in that a suction duct is disposed in the area of the discharge.

30. Apparatus according to claim 16, characterized in that a temperature sensor is disposed in the treatment chamber or in the inlet of the treatment screw conveyor such that the treatment temperature of the material is sensed and the drive of the treatment screw conveyor can be regulated in order to maintain the optimum treatment temperature and treatment time.

* * * * *